United States Patent
Yokoi et al.

(10) Patent No.: US 10,908,143 B2
(45) Date of Patent: Feb. 2, 2021

(54) CURRENT MEASURING DEVICE, CURRENT MEASURING METHOD, AND CURRENT MEASURING KIT

(71) Applicant: Hitachi, Ltd., Tokyo (JP)

(72) Inventors: Takahide Yokoi, Tokyo (JP); Takashi Anazawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 446 days.

(21) Appl. No.: 15/037,420

(22) PCT Filed: Nov. 27, 2013

(86) PCT No.: PCT/JP2013/081834
§ 371 (c)(1),
(2) Date: May 18, 2016

(87) PCT Pub. No.: WO2015/079510
PCT Pub. Date: Jun. 4, 2015

(65) Prior Publication Data
US 2016/0290988 A1    Oct. 6, 2016

(51) Int. Cl.
*G01N 33/487* (2006.01)
*G01N 27/40* (2006.01)
*C12Q 1/6869* (2018.01)

(52) U.S. Cl.
CPC ..... *G01N 33/48721* (2013.01); *C12Q 1/6869* (2013.01); *G01N 27/40* (2013.01)

(58) Field of Classification Search
CPC . G01N 33/48721; G01N 27/40; C12Q 1/6869
See application file for complete search history.

(56) References Cited

U.S. PATENT DOCUMENTS

2006/0262375 A1    11/2006   Ohkubo
2010/0331194 A1    12/2010   Turner et al.
(Continued)

FOREIGN PATENT DOCUMENTS

| JP | 2006-331685 A | 12/2006 |
| JP | 2012-26986 A | 2/2012 |
| JP | 2012026986 A | * 2/2012 |

OTHER PUBLICATIONS

Wanunu et al. (M Wanunu, Nanopores: A journey towards DNA sequencing, Physics of Life Reviews 9 (2012) 125-158). (Year: 2012).*

(Continued)

*Primary Examiner* — Maris R Kessel
*Assistant Examiner* — Joshua L Allen
(74) *Attorney, Agent, or Firm* — Crowell & Moring LLP

(57) ABSTRACT

Conventionally, only a pair of electrodes is provided and nanopores arranged in parallel are connected by an electrolyte solution, and therefore a change in an ion current to be measured is a sum of changes in ion currents generated in the respective nanopores. The invention includes: a first solution chamber including a plurality of first electrodes; a second solution chamber including a second electrode which is a counter electrode of the first electrodes; a membrane provided between the first solution chamber and the second solution chamber, the membrane having a plurality of small holes; a measuring unit for applying a voltage between the first electrodes and the second electrode and measuring a current flowing between the first electrodes and the second electrode via the small holes; and an insulating structure forming unit for forming, in the first solution chamber, an insulating structure for insulating the first electrodes in a state in which a conductive liquid is filled between the small (Continued)

holes and the first electrodes and achieves parallel measurement of ion currents by using nanopores.

6 Claims, 9 Drawing Sheets

(56) References Cited

U.S. PATENT DOCUMENTS

| | | |
|---|---|---|
| 2013/0180867 A1 | 7/2013 | Rosenstein et al. |
| 2014/0034497 A1* | 2/2014 | Davis .............. G01N 27/44791 204/451 |
| 2014/0158540 A1* | 6/2014 | Ohura .............. G01N 33/48721 204/543 |
| 2015/0153302 A1* | 6/2015 | Davis .................. C12Q 1/6869 204/403.08 |

OTHER PUBLICATIONS

Takeshi et al. (JP 2012026986 A, machine translation) (Year: 2012).*
International Search Report (PCT/ISA/210) issued in PCT Application No. PCT/JP2013/081834 dated Jan. 14, 2014 with English translation (Four (4) pages).
Venta, K., et al., "Differentiation of Short, Single-Stranded DNA Homopolymers in Solid-State Nanopores" ACS Nano, 2013, vol. 7, No. 5, pp. 4629-4636 (Eight (8) pages).

* cited by examiner

[FIG. 1]
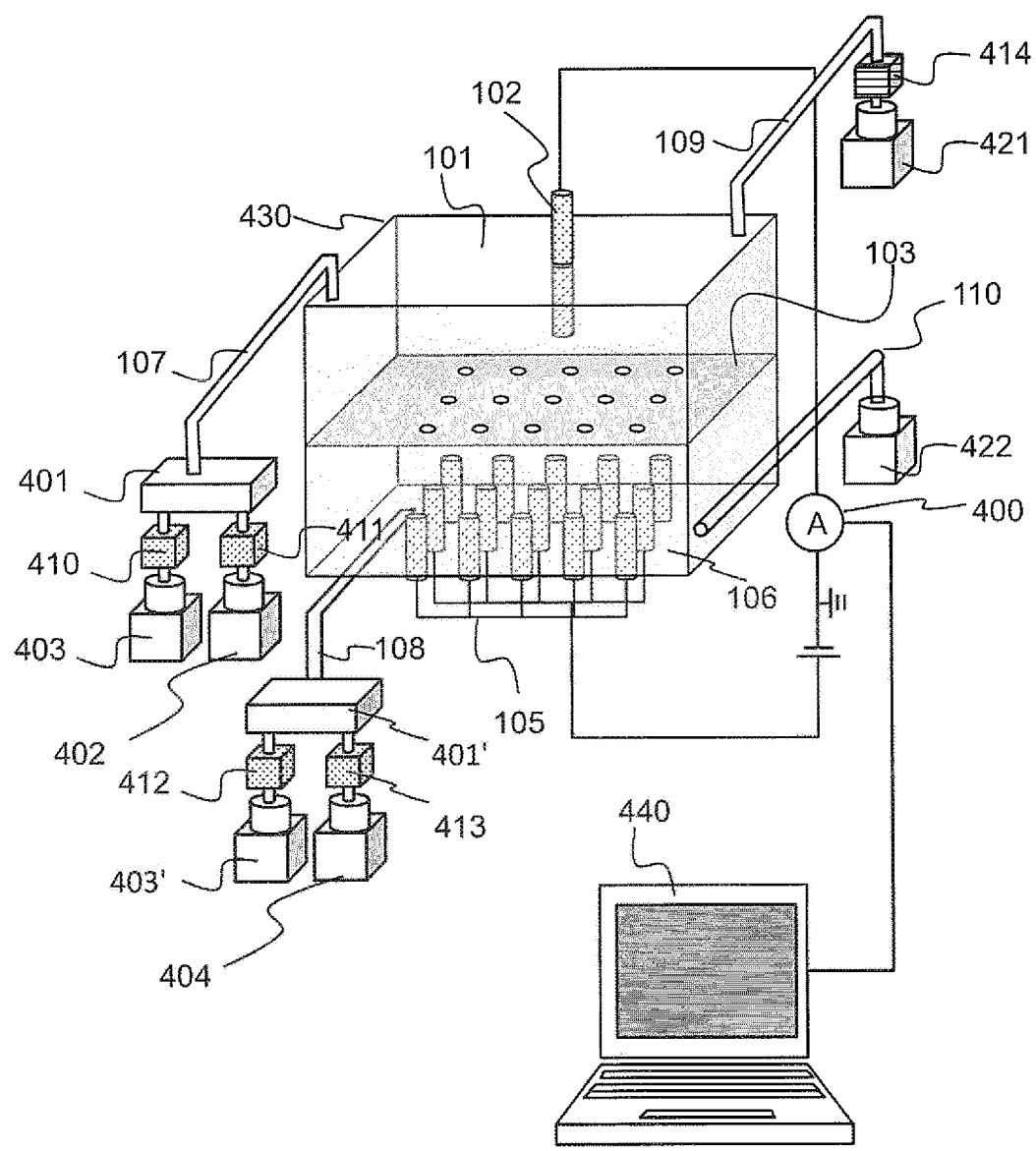

[FIG. 2A]
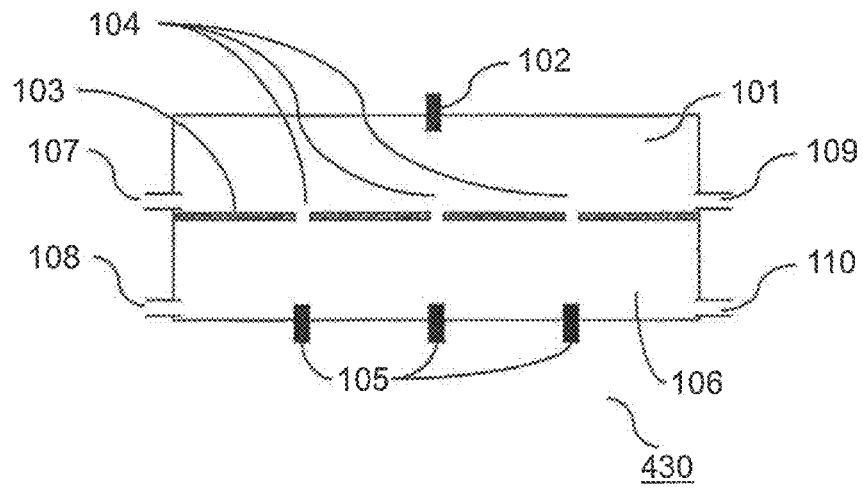
[FIG. 2B]
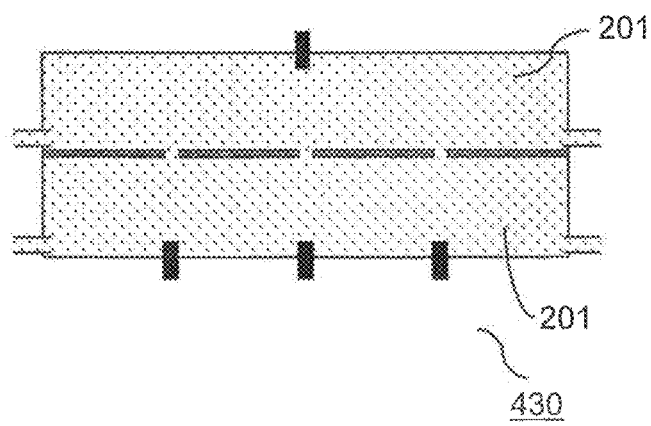
[FIG. 2C]
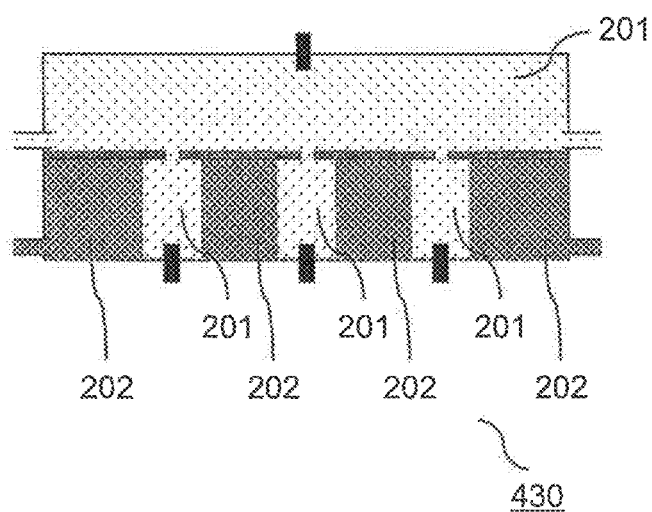

[FIG. 3]
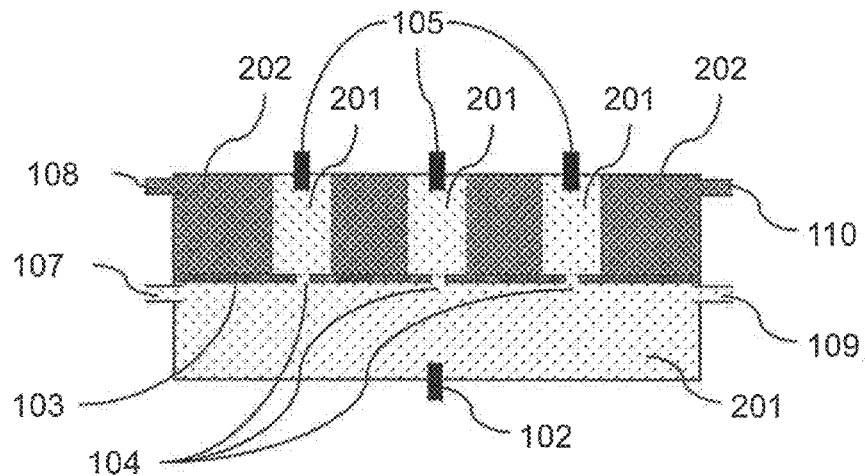
[FIG. 4A]
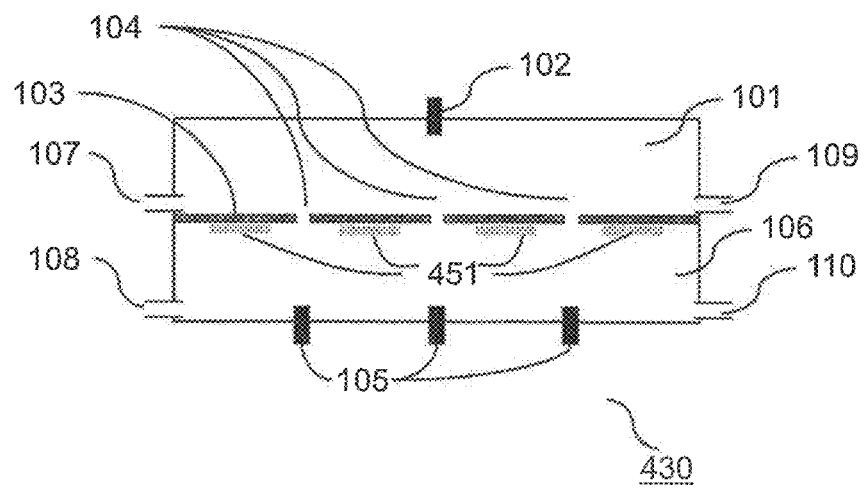
[FIG. 4B]
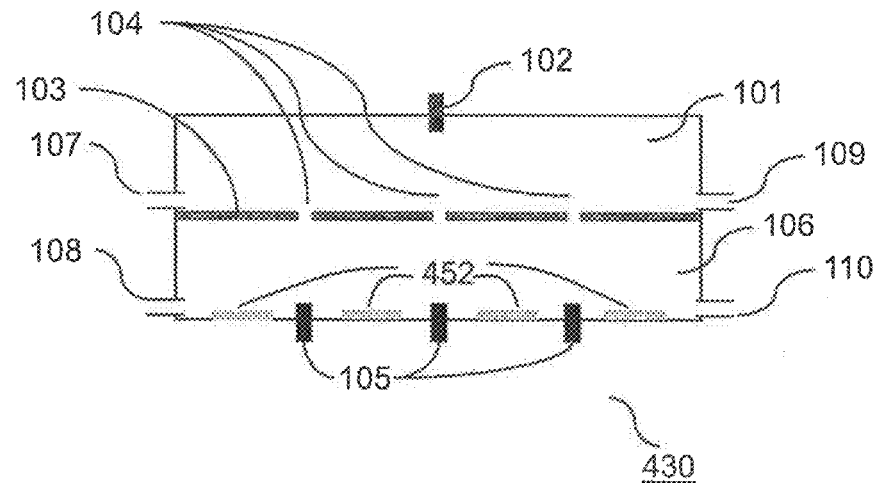

[FIG. 4C]
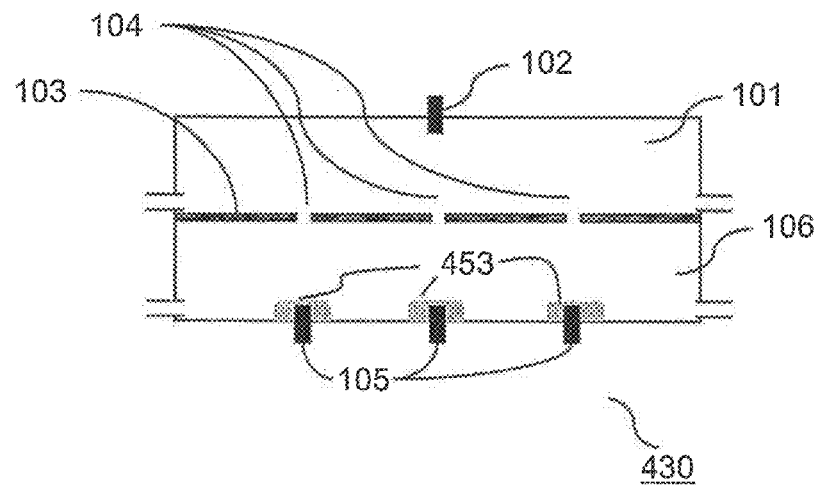
[FIG. 4D]
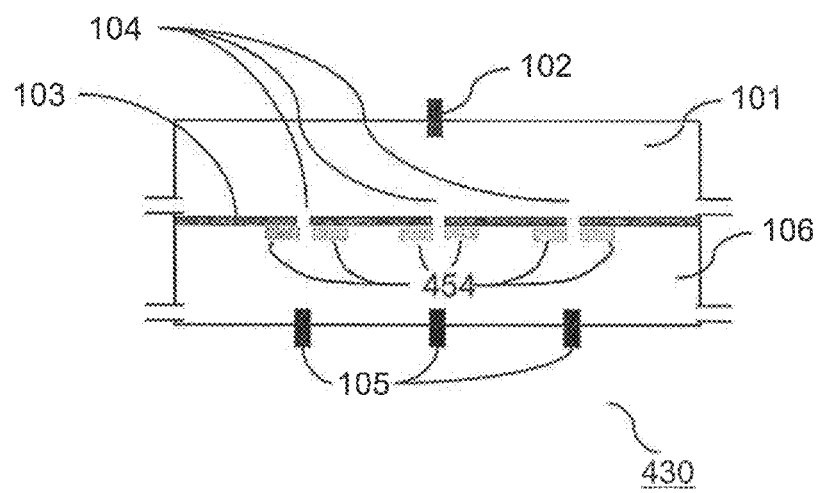
[FIG. 5A]
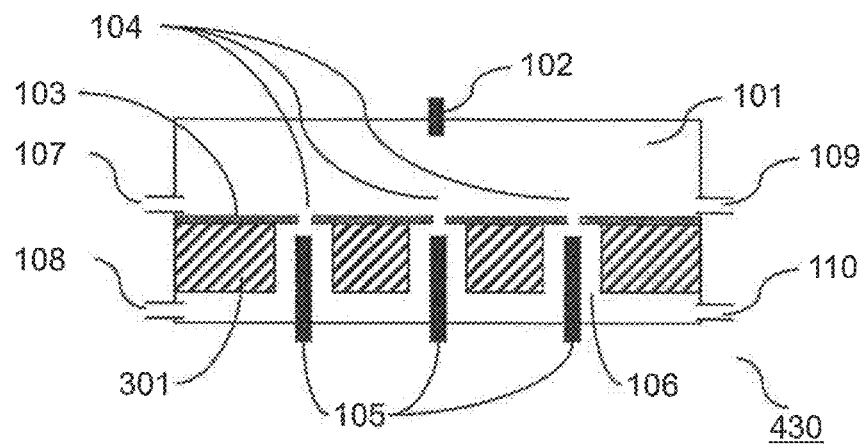

[FIG. 5B]
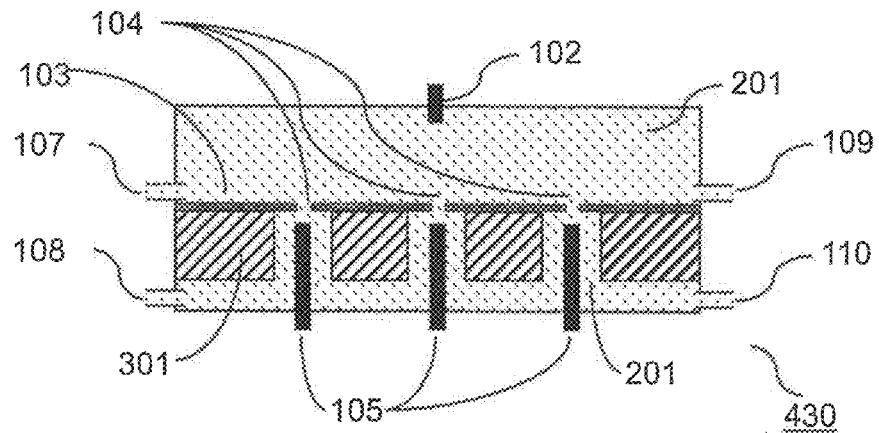
[FIG. 5C]
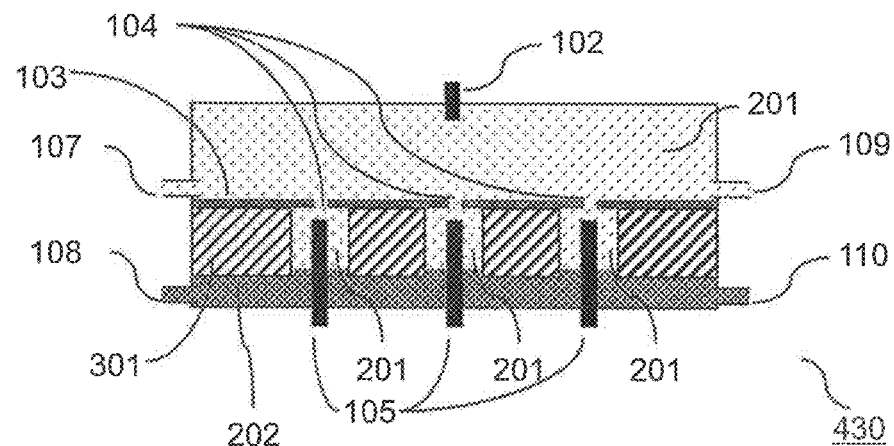
[FIG. 6A]
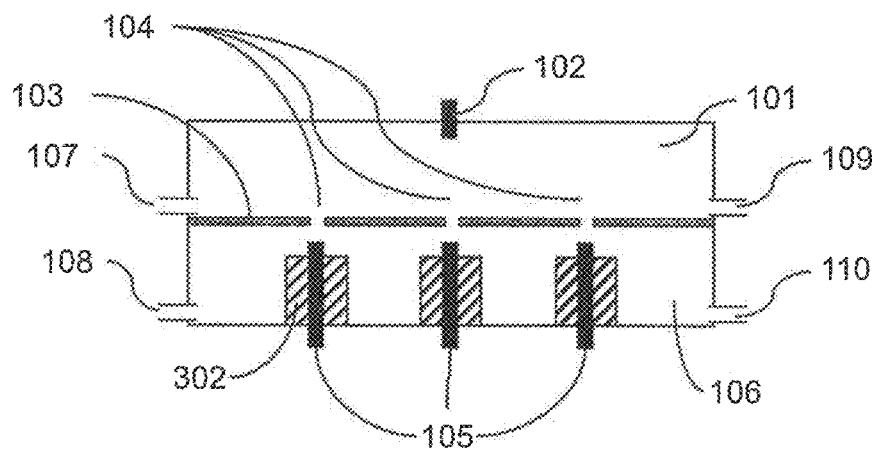

[FIG. 6B]
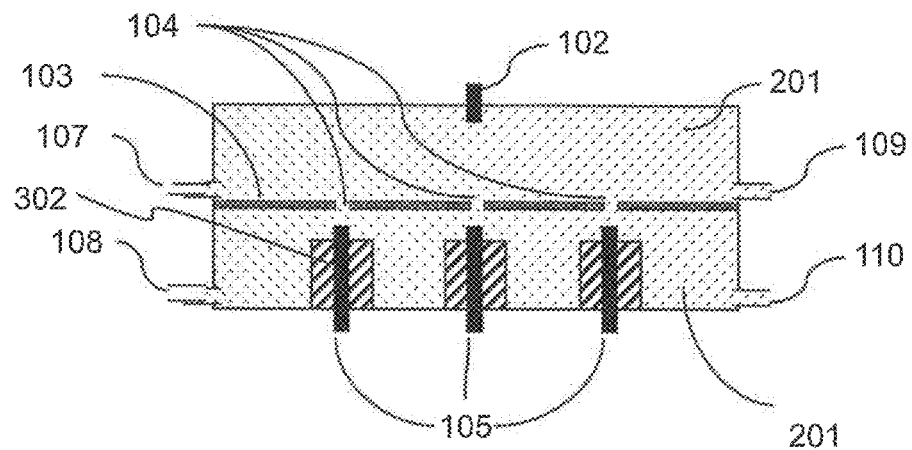
[FIG. 6C]
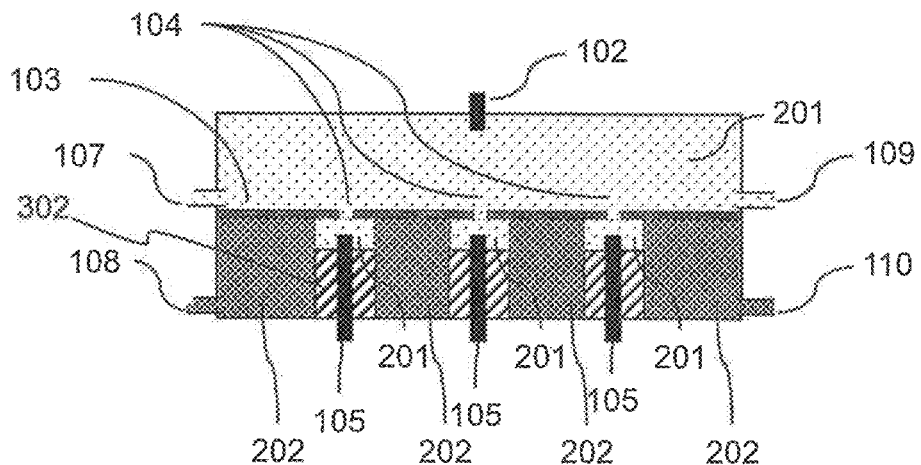
[FIG. 7A]
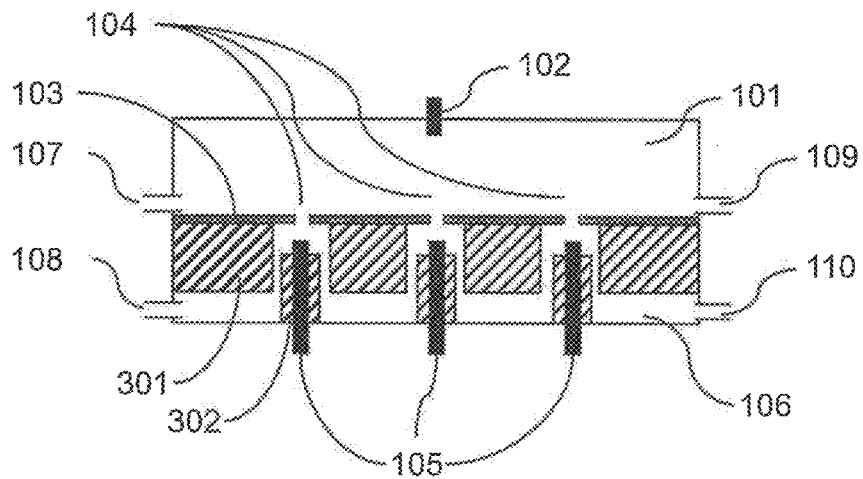

[FIG. 7B]
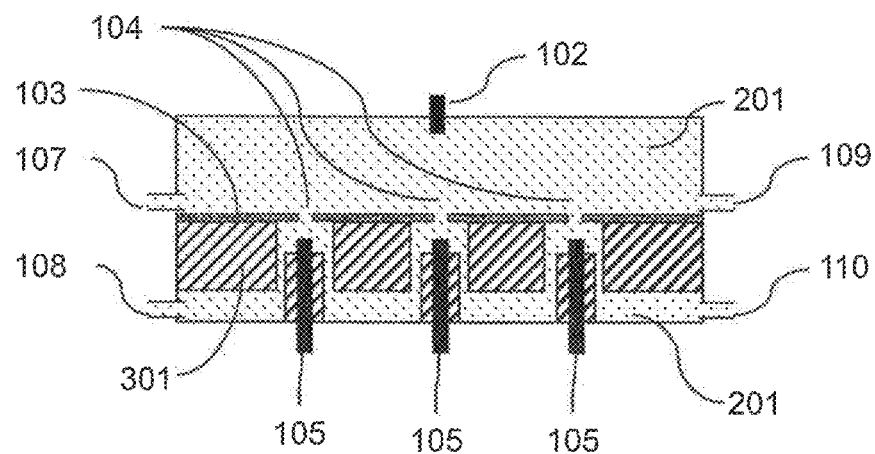
[FIG. 7C]
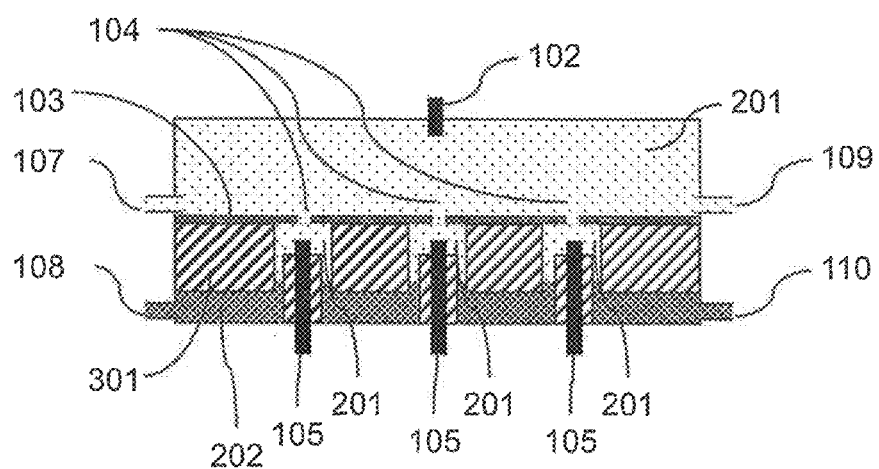
[FIG. 8]
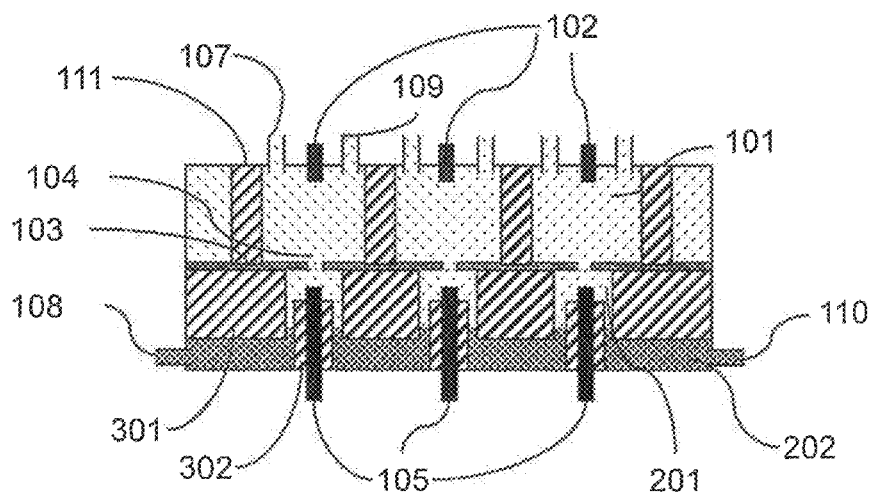

[FIG. 9]
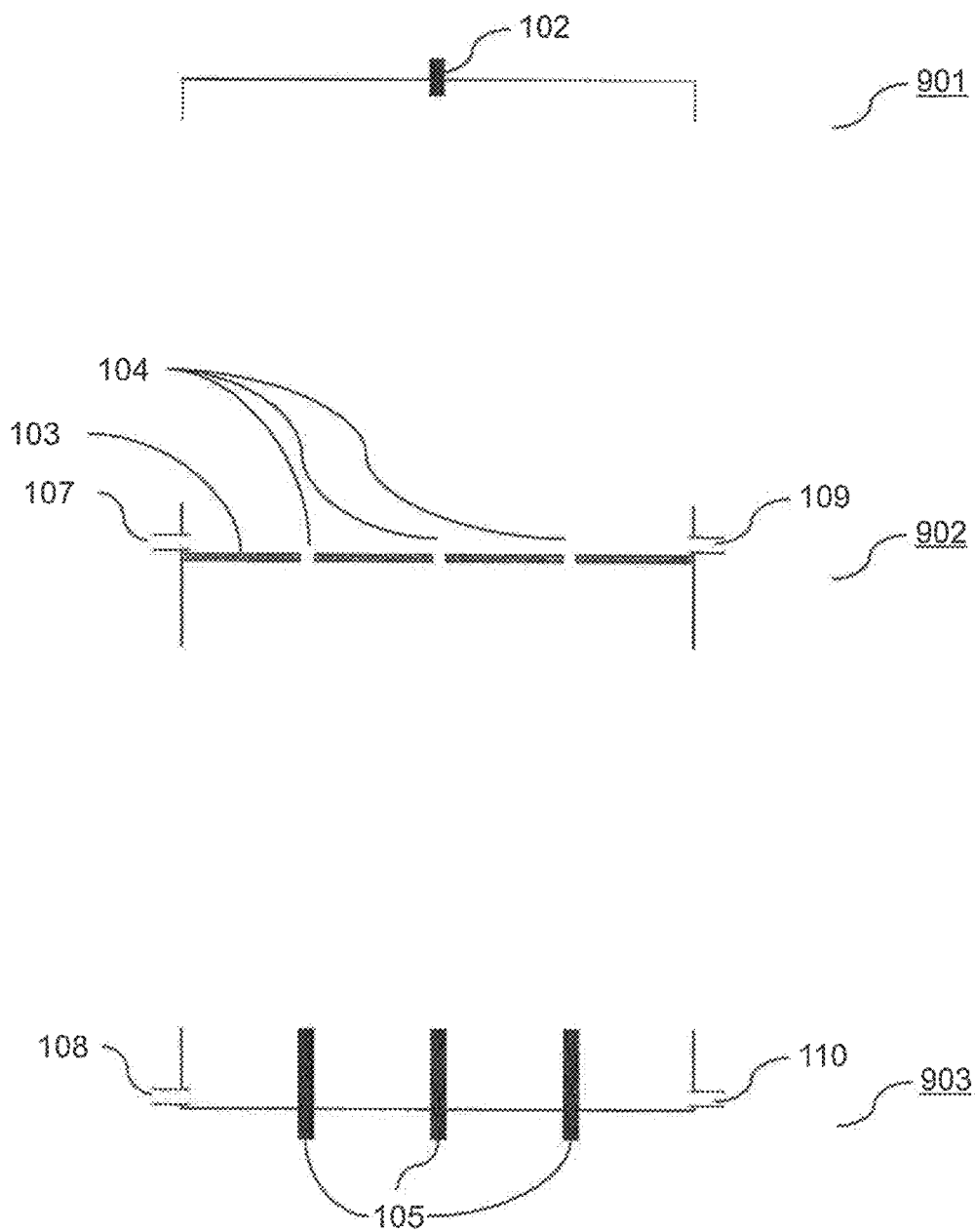

[FIG. 10]
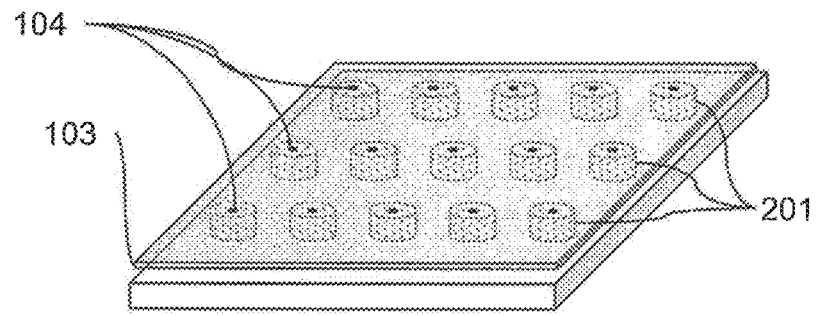
[FIG. 11]
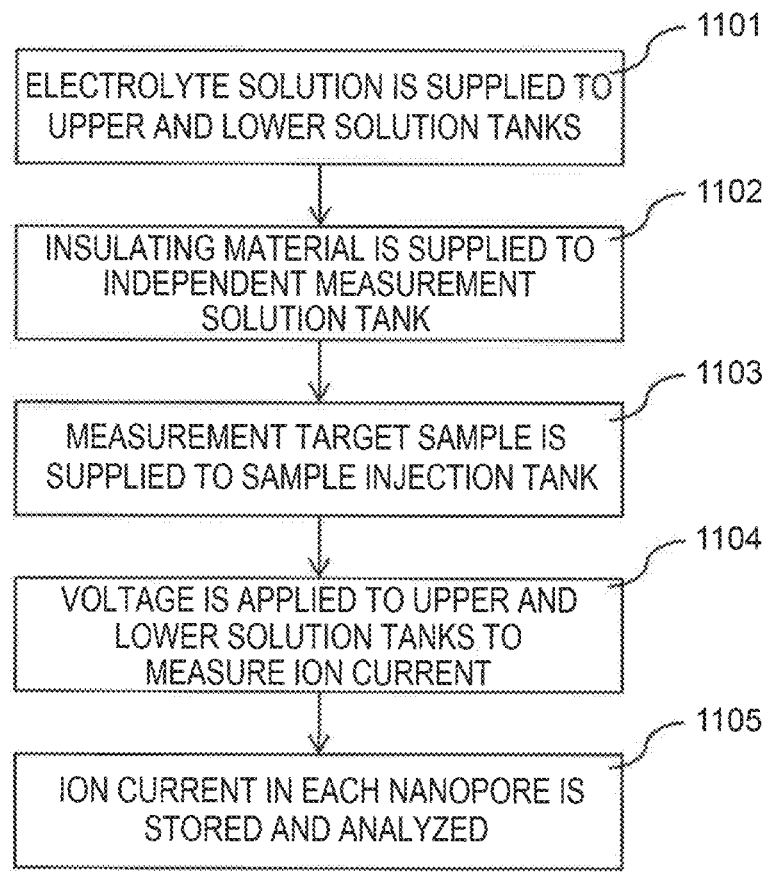

CURRENT MEASURING DEVICE, CURRENT MEASURING METHOD, AND CURRENT MEASURING KIT

TECHNICAL FIELD

The present invention relates to a technology for measuring a current. In particular, the invention relates to a measuring device, a measuring method, and a measuring kit for measuring an ion current by using parallel nanopores.

BACKGROUND ART

In diagnoses of diseases and drug discovery research, biopolymers such as nucleic acids (DNA and RNA) and proteins are important biomarkers. In particular, nucleic acids are a material constituting a genome that carries genetic information, and many genome research institutes study the genome for understanding of individual heterogeneities and analyze cancers physiology. Genomic information of a human contains three billion bases, i.e., an enormous amount of information, and therefore an inexpensive and high-speed analysis device for acquiring genomic information is desired. In view of this, a nanopore sequencer having small holes (nanopores) whose size is substantially as large as that of DNA are attracting the most attention as a new gene analysis technology.

The nanopore sequencer analyzes biopolymers such as DMA and proteins by providing an insulating thin membrane having nanopores between two solution chambers, setting a voltage gradient between both the solution chambers, and measuring an ion current. For example, in the case where a DNA molecule serving as a biopolymer is added to one of the solution chambers, the DMA molecule passes through the nanopore to move to another solution chamber due to the voltage gradient. When the DNA molecule passes through the nanopore, a flow of ions is partially blocked in the nanopore, which results in reduction of a current (ion current). By measuring a magnitude of this ion current and a duration time of the ion current, it is possible to determine kinds of individual bases constituting the DMA molecule that has passed through the nanopore and detect the length of the DNA molecule.

The nanopore sequencer is roughly classified into two types, i.e., a bio-nanopore sequencer disclosed in PTL 1 and a solid nanopore sequencer disclosed in NPL 1. For example, as disclosed in PTL 1, the bio-nanopore sequencer performs analysis using pore forming proteins inserted into a lipid bilayer serving as an insulating membrane. Meanwhile, for example, as disclosed in NPL the solid nanopore sequencer measures an ion current with the use of nanopores formed in a silicon nitride membrane serving as an insulating membrane by using electron beams or the like, instead of using a pore forming proteins.

Although nanopore sequencer has good potentials for genome analysis, sufficient analysis throughput cannot be obtained with a single nanopore. Therefore, in order to put measuring devices into practical use, it is desirable to improve the analysis throughput by arranging a plurality of nanopores in parallel. PTL 1 discloses the bio-nanopore sequencer having a configuration in which bio-nanopores are arranged in parallel.

CITATION LIST

Patent Literature

[PTL 1] U.S. patent application No. 2010/0331194

Non Patent Literature

[NPL 1] Venta et al. ACS Nano, 2013, 7 (5), pp 4629-4636

SUMMARY OF INVENTION

Technical Problems

In the conventional nanopore sequencer disclosed in PTL 1 described above, a plurality of nanopores exist but only a pair of electrodes is provided and the nanopores arranged in parallel are connected by an electrolyte solution. With this configuration, a change in an ion current to be measured is a sum of changes in ion currents generated in the respective nanopores, and therefore it is difficult to detect a change in an ion current generated in each nanopore.

In view of the above problems, in order to achieve parallel measurement of ion currents by using nanopores, an object of the invention is to individually measure ion currents generated in a plurality of respective nanopores existing in a thin membrane.

Solution to Problems

An embodiment of the present invention to solve at least one of the above problems includes; a first solution chambers including a plurality of first electrodes; a second solution chamber including a second electrode which is a counter electrode of the first electrodes; a membrane provided between the first solution chambers and the second solution chamber, the membrane having a plurality of small holes; a measuring unit for applying a voltage between the first electrodes and the second electrode and measuring a current flowing between the first electrodes and the second electrode via the small holes; and an insulating structure forming unit for forming, in the first, solution chamber, an insulating structure for insulating the first electrodes in a state in which a conductive liquid is filled between the small holes and the first electrodes.

Advantageous Effects of Invention

According to the invention, when ion currents generated in a plurality of respective nanopores existing in a thin membrane are individually measured, it is possible to achieve parallel measurement of ion currents by using nanopores.

BRIEF DESCRIPTION OF DRAWINGS

FIG. 1 is a schematic view of an example of a parallel ion current measuring device in the invention.

FIG. 2A illustrates a configuration example of a solution chamber in Example 1 (before a solution is supplied).

FIG. 2B illustrates a configuration example of the solution chamber in Example 1 (after an electrolyte solution is supplied).

FIG. 2C illustrates a configuration example of the solution chamber in Example 1 (after insulation is constructed).

FIG. 3 illustrates another configuration example of the solution chamber in Example 1 (after insulation is constructed).

FIG. 4A illustrates a configuration example of an insulation forming mechanism (hydrophobic treatment) in Example 1.

FIG. 4B illustrates another configuration example of the insulation forming mechanism (hydrophobic treatment) in Example 1.

FIG. 4C illustrates a configuration example of the insulation forming mechanism (hydrophilic treatment) in Example 1.

FIG. 4D illustrates another configuration example of the insulation forming mechanism (hydrophilic treatment) in Example 1.

FIG. 5A illustrates a configuration example of a solution chamber in Example 2 (before a solution is supplied).

FIG. 5B illustrates a configuration example of the solution chamber in Example 2 (after an electrolyte solution is supplied).

FIG. 5C illustrates a configuration example of the solution chamber in Example 2 (after insulation is constructed).

FIG. 6A illustrates a configuration example of a solution chamber in Example 3 (before a solution is supplied).

FIG. 6B illustrates a configuration example of the solution chamber in Example 3 (after an electrolyte solution is supplied).

FIG. 6C illustrates a configuration example of the solution chamber in Example 3 (after insulation is constructed).

FIG. 7A illustrates a configuration example of a solution chamber in Example 4 (before a solution is supplied).

FIG. 7B illustrates a configuration example of the solution chamber in Example 4 (after an electrolyte solution is supplied).

FIG. 7C illustrates a configuration example of the solution chamber in Example 4 (after insulation is constructed).

FIG. 8 illustrates a configuration example of a solution chamber in Example 5 (after insulation is constructed).

FIG. 9 illustrates a configuration example of a parallel ion current measuring kit in the invention.

FIG. 10 is a bird's-eye view of an independent measurement electrode chamber in which insulation has been formed between electrodes.

FIG. 11 is a flowchart showing an example of measurement processing of a parallel ion current measuring device in the invention.

DESCRIPTION OF EMBODIMENTS

Hereinafter, an embodiment, of the invention will be described with reference to the drawings, Note that this embodiment is merely an example to achieve the invention, and the invention is not limited thereto. In this embodiment, in order to measure individual ion currents generated in individual nanopores, individual electrodes corresponding to the respective nanopores are provided and insulation is performed between those electrodes in at least one solution chamber. Then, in the solution chamber in which the plurality of electrodes exist, an electrolyte solution for connecting the nanopores and the electrodes in one-to-one correspondence is formed to separate the electrodes arranged in parallel, thereby achieving insulation between the electrodes.

Herein, the nanopore described in this embodiment means a nanosize hole provided in a thin membrane to penetrate the thin membrane between a front side and a back side thereof. Further, in this embodiment, a solution chamber in which a plurality of electrodes which need to be subjected to the above insulation are arranged is referred to as an independent measurement electrode chamber, and a solution chamber connected to the independent measurement electrode chamber via nanopores, in which at least one counter electrode of the electrodes of the independent measurement electrode chamber is arranged, is referred to as a sample injection chamber. Hereinafter, this embodiment will be described by exemplifying more detailed examples.

EXAMPLE 1

A configuration example of a parallel ion current measuring device in this example will be described with reference to FIG. 1. The ion current parallel measuring device in this example for measuring ion currents in respective nanopores arranged in parallel includes a solution chamber 430 including an insulating membrane 103 having the nanopores, electrodes (102, 105), inlet ports (107, 108), and outlet ports (109, 110), electrolyte containers (403, 403'), a sample solution container 402, an insulating material container 404, valves (410, 411, 412, 413, 414), pumps (401, 401'), waste liquid containers (421, 422), a voltage application unit 400, and a control/storage unit 440 for controlling supply of a solution, measurement of an ion current, and the like. Herein, the solution chamber 430 is divided into two regions by the insulating membrane 103, i.e., a sample injection chamber 101 and an independent measurement electrode chamber 106. Control and the like in the control/storage unit 440 described below can be realized by software by forming a program that realizes a part or all thereof, and, needless to say, the control and the like can be realized by hardware by, for example, designing a part or all thereof with an integrated circuit.

A configuration example of the solution chamber 430 will be described with reference to FIG. 2A. As illustrated in FIG. 2A, the solution chamber 430 includes the insulating membrane 103, a plurality of nanopores 104 existing in the insulating membrane 103, the independent measurement electrode chamber 106 in which the electrodes 105 corresponding one-to-one to the individual nanopores 104 are arranged, and the sample injection chamber 101 in which at least one electrode 102 serving as a counter electrode of the electrodes 105 in the independent measurement electrode chamber 106 is arranged. Furthermore, the sample injection chamber 101 and the independent measurement electrode chamber 106 have inlet ports (107, 108) for filling a material and outlet ports (109, 110) for discharging a surplus material. The inlet ports (107, 108) and the outlet ports (109, 110) may be arranged in an upper surface or a lower surface of the solution chamber, and the number of arranged ports is not limited to the ports illustrated in FIG. 2A.

Herein, the sample injection chamber 101 and the independent measurement electrode chamber 106 are connected via the nanopores 104. As described below, at the time of measurement, the electrode 102 of the sample injection chamber 101 and the electrodes 105 of the independent measurement electrode chamber 106 are connected via the nanopores 104 by an electrolyte solution. Note that the sample injection chamber 101 may be one solution chamber even at the time of measurement because the sample injection chamber 101 is not required to be divided in the unit of nanopore. Further, one or plural electrodes 102 may be arranged.

Measurement of an ion current based on control performed by the control/storage unit 440 in the parallel ion current measuring device in this example will be described with reference to FIG. 11.

First, an aqueous electrolyte solution is supplied to both of the sample injection chamber 101 and the independent measurement electrode chamber 106 (1101). As described above, the solution chamber 430 has one or more inlet ports (107, 108), and the electrolyte solution is supplied from the electrolyte containers (403, 403') by driving force of the pumps (401, 401'). In this example, the kind and concentration of the electrolyte solution in the sample injection chamber 101 may be the same as or different from those of the electrolyte solution in the independent measurement electrode chamber 106. Then, an insulating material is supplied to the independent measurement electrode chamber 106 in which the plurality of electrodes 105 are arranged from the insulating material container 404 to insulate the electrodes 105 (1102). Note that the electrolyte solution replaced when the insulating material is supplied to the independent measurement electrode chamber is discharged to the waste liquid container 422 via the outlet port 110.

Herein, details of a step of forming portions of the electrolyte solution isolated from each other, which have been described in 1101 to 1102 in FIG. 11, will be described with reference to FIG. 2A, FIG. 2B, and FIG. 2C. In a state before the solution is added, which is illustrated in FIG. 2A, the independent measurement electrode chamber 106 is a continuous space, and a structure for physically separating the plurality of provided electrodes 105 does not exist. By supply of the electrolyte solution to the sample injection chamber 101 and the independent measurement electrode chamber 106 described in 1101, the sample injection chamber 101 and the independent measurement electrode chamber 106 are filled with an electrolyte solution 201 via the nanopores 104 as illustrated in FIG. 2B. Then, as described in 1102, an insulating material is supplied to the independent measurement electrode chamber via the inlet port 108 of the independent measurement electrode chamber 106 so as to be replaced with the electrolyte solution, and therefore, as illustrated in FIG. 2C, each combination of the nanopore 104 and the corresponding electrode 105 is isolated by an insulating material 202 from another combination of the nanopore 104 and the electrode 105. Thus, insulation between the electrodes is achieved.

This insulation between the electrodes is achieved by constructing, in the independent measurement electrode chamber 106, regions whose hydrophilicity/hydrophobicity are different due to selection of a material or coating on a surface and controlling a region in which the electrolyte solution 201 remains and a region filled with the insulating material 202 by using a difference between affinities of a material/surface and the electrolyte solution 201 and the insulating material 202. Details of an insulation forming mechanism between the electrodes 105 in this example will be described below with reference to FIG. 4A, FIG. 4B, FIG. 4C, and FIG. 4D.

FIG. 10 is a bird's-eye view illustrating a state of the independent measurement electrode chamber 106 in which insulation between the electrodes 105 has been formed by using an insulating material. The plurality of nanopores 104 exist in the insulating membrane 103, and the nanopores 104 and the electrodes 105 are connected, respectively, by portions of the electrolyte solution 201 isolated from each other. Note that the configurations in FIG. 2A, FIG. 2B, FIG. 2C, and FIG. 10 are examples applied to the case where a liquid density of a fluidic insulating material is larger than that of an electrolyte solution. However, in the case where the liquid density of the insulating material is smaller than that of the electrolyte solution, as illustrated in FIG. 3, arrangement of the electrodes and a configuration of the solution chamber can be provided upside down in accordance with the liquid density of the insulating material.

When the electrolyte solution and the insulating material are supplied as in 1101 to 1102 as described above, the electrode 102 of the sample injection chamber 101 and the electrodes 105 of the independent measurement electrode chamber 106 are connected via the nanopores by the electrolyte solution in a state in which the plurality of electrodes 105 provided in the independent measurement electrode chamber 106 are insulated by the insulating material supplied from the insulating material containers 404. With this, an ion current can be measured.

Referring back to FIG. 11, processing after completion of insulation in the independent measurement electrode chamber 106 will be described. After the above insulation is completed, sample is supplied to the sample injection chamber 101 (1103). An aqueous sample including a biopolymer such as a DMA molecule serving as a measurement target material is supplied to the sample injection chamber 101 from the sample solution container 402. Note that, although supply of the sample to the sample injection chamber 101 is desirably performed, after insulation in the independent measurement electrode chamber 106 is achieved, supply of the sample can also be performed before insulation in the independent measurement electrode chamber 106 is achieved. In the sample injection chamber 101, not only the inlet port 107 but also one or more outlet ports 109 are provided, and a surplus electrolyte solution and insulating material are discharged to the waste liquid container 421.

After the electrodes are insulated and the sample is supplied, a voltage is then applied, to both the solution chambers to measure an ion current (1104). When the voltage application unit 400 applies a voltage between the electrode 102 and the electrodes 105, an ion current is generated in the nanopores 104 arranged in parallel in the insulating membrane 103. Then, a change in an ion current level generated when the biopolymer passes through each of the individual nanopores arranged in parallel is independently measured for each of the nanopores by using the electrodes provided in both the solution chambers. Then, the control/storage unit 440 records and analyzes the measured ion current value in each nanopore (1105).

By the above processing in the parallel ion current measuring device in this example, it is possible to measure individual ion currents generated in the individual nanopores 104. Hereinafter, the insulation forming mechanism between the electrodes 105 in the independent measurement electrode chamber 106 in this example will be described in more detail. Note that, as the insulation forming mechanism, the inlet port 108, the outlet port 110, and regions 451 and 452 having high hydrophobicity or regions 453 and 454 having high hydrophilicity described below are provided in the solution chamber 430 in this example. In the parallel ion current measuring device illustrated in FIG. 1, the insulation forming mechanism includes the insulating material container 404, the valve 413, and the pump 401' in addition to the above members. However, the valve 413 and the pump 401' are not limited thereto as long as mechanisms having similar functions are provided.

As illustrated in FIG. 2C, when the insulation forming mechanism in this example performs arrangement control of the aqueous electrolyte solution 201 and the insulating material 202 by using a difference in hydrophilicity/hydrophobicity of materials in the independent measurement electrode chamber 106, the portions of the electrolyte solution 201 are limited to regions connecting the nanopores 104 and the electrodes 105 in the independent measurement electrode chamber 106.

As an example of the above configuration to cause the electrolyte solution to remain, a region in which the electrolyte solution remains is limited by using a material having hydrophobicity for a surface of the independent measurement electrode chamber 106 to be brought into contact with the insulating material or by coating a hydrophobic material on the surface. That is, as illustrated in FIG. 4A, the regions 451 having higher hydrophobicity than that of portions around the individual nanopores are provided between the adjacent nanopores 104 in the insulating membrane 103 facing the independent measurement electrode chamber 106 by using a material having hydrophobicity or by coating a hydrophobic material. Further, as illustrated in FIG. 4B, the regions 452 having higher hydrophobicity than that of portions around the individual electrodes may be provided between the electrodes 105 arranged in parallel in the independent measurement electrode chamber 106 by using a material having hydrophobicity or by coating a hydrophobic material. Furthermore, a surface of the independent measurement chamber may be a region having higher hydrophobicity than that of the electrodes 105 arranged in parallel.

Another example of the configuration to cause the electrolyte solution to remain, the region in which the electrolyte solution remains may be limited by using a material having hydrophilicity for a surface of the independent measurement electrode chamber 106 to be brought into contact with an insulating material or by coating a hydrophilic material on the surface. In other words, the region in which the electrolyte solution remains is limited by using a material having high hydrophilicity for the electrodes 105 or by performing hydrophilic treatment on measurement electrodes and a surrounding substrate including the electrodes to provide the hydrophilic regions 453 as illustrated in FIG. 4C. Further, as illustrated in FIG. 4D, the hydrophilic regions 454 may be provided by partially performing hydrophilic treatment on the insulating membrane in which the nanopores corresponding to the respective measurement electrodes exist. Alternatively, both the hydrophilic regions 453 and 454 may be provided by performing hydrophilic treatment on both the electrode side and the nanopore side.

As described above, when the region in which the electrolyte solution 201 remains is limited by using a difference in hydrophobicity/hydrophilicity caused by selection of a material or coating on a surface, i.e., by using a difference between affinities of the material and the electrolyte solution 201 or the insulating material 202, remaining of the electrolyte solution 201 connects the nanopores 104 and the electrodes 105, and the insulating material 202 insulates the electrodes 105. In the above configuration that limits the region in which the electrolyte solution remains, insulation between the electrodes is achieved by performing arrangement control so that the electrolyte solution is isolated. The hydrophobic region and the hydrophilic region may be simultaneously provided in the same device, may be individually provided, or may be selectively combined.

Herein, an example of the insulating material 202 in this example will be described. The insulating material 202 for use in isolation of the electrolyte solution 201 is an insulating material that is fluidic in coexistence with the electrolyte solution 201 at least when the insulating material is fed to the independent measurement electrode chamber 106 via the inlet port 108. A more preferable condition, of the insulating material 202 is that the insulating material has a melting point between a boiling point and a freezing point of the electrolyte solution. Examples of the material that satisfies the above conditions in measurement of an ion current using nanopores encompass insulating oil, rubber-based polymer, silicone gel, and resin. Further, gas is also usable as the material that can be applied to isolate the electrolyte solution.

Fluidity is a property that is necessary for a step of supplying the insulating material to the independent measurement electrode chamber 106, and therefore, after this supply step is completed, the insulating material 202 can be solidified by, for example, temperature reduction processing to eliminate the fluidity. In a state in which the insulating material 202 is solidified, the electrolyte solution 201 is isolated by such a solid partition wall, and, because of existence of the solid partition wall, an isolation structure of the electrolyte solution can be kept more stably when this device receives an impact such as vibration or device handling. This is significantly advantageous. In order to solidify the insulating material by reducing a temperature thereof as in the above example, a mechanism for controlling the temperature on the basis of control performed by the control/storage unit 440 can be provided, or the whole device can be placed in, for example, a low-temperature environment such as a refrigerator. Further, solidifying the insulating material by reducing the temperature thereof is merely a form of this example, and therefore whether to implement solidification and a solidification method are not limited to the above example.

A configuration example of a measuring kit for the parallel ion current measuring device in this example will be described with reference to FIG. 9. This kit manufactured by a fine processing technology is roughly classified into the following three function units on the basis of functions and manufacturing steps: a sample injection chamber constituent member 901 for constituting the sample injection chamber 101, in which the electrode 102 is arranged; a main body member 902 having an insulating membrane in which nanopores are arranged; and an independent measurement; electrode chamber constituent member 903 for constituting the independent measurement electrode chamber, in which the plurality of electrodes 105 are arranged. Herein, arrangement positions and the numbers of the inlet ports (107, 108) and the outlet ports (109, 110) can be changed as appropriate in accordance with an object.

The kit may be a kit obtained by integrating any one of the sample injection chamber constituent member 901 and the independent measurement electrode chamber constituent member 903 with the main body member 902 or a kit obtained by forming the sample injection chamber constituent member 301, the main body member 902, and the independent measurement electrode chamber constituent member 903 as one member in advance. In other words, the sample injection chamber constituent member 901, the main body member 902, and the independent measurement electrode chamber constituent member 903, which are constituent elements of this kit, are different from one another in manufacturing costs and durability, and therefore the function units can be individually selected, to be repeatedly used, depending on an object of a user, and the function units can be individually provided for such a user. Further, not only the members illustrated in FIG. 9 but also the electrolyte solution and the insulating material used at the time of measurement and a cleaning solution for the solution chamber can be combined to be provided as a measuring kit. This is desirable for stable measurement.

Hereinafter, an effect exerted by parallel arrangement of the nanopores in this example will be described. In the case where measurement electrodes are arranged, in parallel in one solution chamber serving as an independent measurement electrode chamber, whereas a measurement electrode is provided in the other solution chamber serving as a sample injection solution chamber, and a fixed physical partition wall for insulating the measurement electrodes arranged in parallel in the independent measurement electrode chamber is constructed, individual independent measurement electrode chambers that are physically isolated are connected to the sample injection solution chamber via the nanopores but are substantially closed spaces. Therefore, it is difficult to fill the inside of each of the independent measurement electrode chambers with the electrolyte solution. On the contrary, in the measuring device for measuring an ion current according to this example, supply of the electrolyte solution to the individual electrodes arranged in parallel in the independent measurement electrode chamber and insulation between the parallel electrodes can be simultaneously achieved in a preferable condition in terms of parallel arrangement of the nanopores.

In other words, with the configuration in this example, insulation between the individual electrodes corresponding to the respective nanopores can be easily achieved by filling the single independent measurement electrode chamber 106 with the electrolyte solution 201 and then inlet a fluidic insulating material, instead of providing a plurality of independent electrolyte containers in the unit of nanopores and electrodes and filling each electrolyte container with an electrolyte solution by using a complicated solution injection mechanism. In addition, when insulation of the individual nanopores is secured, an ion current in each nanopore can be measured with high accuracy. With this, a processing ability is improved by parallel arrangement of the nanopores.

EXAMPLE 2

In this example, as another form of the insulation forming mechanism for providing the electrolyte solution only in the regions in which the nanopores and the electrodes are connected, a configuration example that modifies a structure around the electrodes and the nanopores in the solution chamber 430 of the parallel ion current measuring device will be described with reference to FIG. 1. Note that the description of the same configurations of the parallel ion current measuring device and the measuring kit as the configurations thereof in Example 1 is omitted, and only a configuration different from the configuration in Example 1, such as a configuration of the insulation forming mechanism, will be described.

In the solution chamber 430 in this example, the inlet port 108, the outlet port 110, and partial partition walls 301 described below are provided as the insulation forming mechanism. In the parallel ion current measuring device illustrated in FIG. 1, the insulation forming mechanism includes the insulating material container 404, the valve 413, and the pump 401' in addition to the above members. However, the valve 413 and the pump 401' are not limited thereto as long as mechanisms having similar functions are provided.

In this example, as illustrated in FIG. 5A, the physical partial partition walls 301 for partially dividing the independent measurement electrode chamber are provided around the individual nanopores 104. FIG. 5B illustrates a state in which the electrolyte solution 201 is added to both the solution chambers. When the insulating material is supplied via the inlet port 108 after the electrolyte solution 201 is supplied, independent portions of the electrolyte solution connecting the individual nanopores and the electrodes are formed as illustrated in FIG. 5C.

An example of a material of the partial partition wall 301 encompasses silicon oxide ($SiO_2$) that is generally used in the fine processing technology. Silicon oxide ($SiO_2$) is a material having high hydrophilicity and is therefore preferable as the material of the partial partition wall 301. When the partial partition walls are made of a hydrophilic material, separation of the electrolyte solution is achieved without performing hydrophilic treatment on a surface of the material. In the case where a material whose liquid density is larger than that of the electrolyte solution is selected as the insulating material, separation of the electrolyte solution is performed by supplying the insulating material via the inlet port 108 in a laminar flow until the partial partition walls have a height to isolate the individual portions of the electrolyte solution. As in Example 1, selection of a hydrophilic/hydrophobic material and partial hydrophilic/hydrophobic treatment are effective. Further, a method using a difference between the liquid density of the insulating material and the electrolyte solution is similar to the method described in Example 1.

EXAMPLE 3

In this example, as another form for providing the electrolyte solution only in the regions in which the nanopores and the electrodes are connected, projecting structures are provided on a substrate around the electrodes 105 in the solution chamber 430 of the parallel ion current measuring device described with reference to FIG. 1. In this example, the description of the same configurations of the parallel ion current measuring device and the measuring kit as the configurations thereof in Example 1 is omitted, and only a configuration different from the configuration in Example 1, such as a configuration of the insulation forming mechanism, will be described.

Note that, in the solution chamber 430 in this example, the inlet port 108, the outlet port 110, and projecting structures 302 described below are provided as the insulation forming mechanism. In the parallel ion current measuring device illustrated in FIG. 1, the insulation forming mechanism includes the insulating material container 404, the valve 413, and the pump 401' in addition to the above members. However, the valve 413 and the pump 401' are not limited thereto as long as mechanisms having similar functions are provided.

In this example, as illustrated in FIG. 6A, the measurement electrodes 105 corresponding to the nanopores 104 are provided on the projecting structures 302 with respect to the substrate. FIG. 6B illustrates a state in which the electrolyte solution is added to both the solution chambers 106 and 101. When the insulating material is supplied via the inlet port 108 after the electrolyte solution is supplied, independent portions of the electrolyte solution connecting the individual nanopores 104 and the electrodes 105 are formed as illustrated in FIG. 6C. Because a distance between the nanopores and the electrodes is reduced by the projecting structures 302, the electrolyte solution remains between the nanopores and the electrodes even after the insulating material is added, and therefore an electrolyte solution chamber in which the nanopores and the electrodes are in one-to-one correspondence can be formed.

In this configuration, insulation in the electrolyte solution chamber is performed by using a property of the electrolyte solution that remains between the nanopores and the electrodes, and therefore an intended insulation between the electrodes can be achieved by excessively supplying the insulating material and discharging a surplus amount thereof via the outlet hole. As in Example 1, selection of a hydrophilic/hydrophobic material and partial hydrophilic/hydrophobic treatment are effective. Further, a method using a difference between the liquid densities of the insulating material and the electrolyte solution is similar to the method described in Example 1.

EXAMPLE 4

In this example, as another form for providing the electrolyte solution only in the regions in which the nanopores and the electrodes are connected, a configuration example obtained by combining the configurations described, in Example 2 and Example 3 will be described. In this example, the description of the same configurations of the parallel ion current measuring device and the measuring kit as the configurations thereof in Example 1 is omitted, and only a configuration different from the configuration in Example 1, such as a configuration of the insulation forming mechanism, will be described.

Note that, in the solution chamber 430 in this example, the inlet port 108, the outlet port 110, the partial partition walls 301, and the projecting structures 302 are provided as the insulation forming mechanism. In the parallel ion current measuring device illustrated in FIG. 1, the insulation forming mechanism includes the insulating material container 404, the valve 413, and the pump 401' in addition to the above members. However, the valve 413 and the pump 401' are not limited thereto as long as mechanisms having similar functions are provided.

In this example, as illustrated in FIG. 7A, the partial partition walls exist immediately below the nanopores 104, and the measurement electrodes 105 are provided on the projecting structures 302 with respect to the substrate. FIG. 7B illustrates a state in which the electrolyte solution is added to both the solution chambers. When the insulating material is supplied via the inlet port 108 after the electrolyte solution is supplied, independent portions of the electrolyte solution connecting the individual nanopores and the electrodes are formed as illustrated in FIG. 7C. As in the description in FIG. 5, selection of a hydrophilic material and partial hydrophilic treatment are effective. As in Example 1, selection of a hydrophilic/hydrophobic material and partial hydrophilic/hydrophobic treatment are effective. Further, a method using a difference between the liquid densities of the insulating material and the electrolyte solution is similar to the method described in Example 1.

EXAMPLE 5

In this example, as another form for providing the electrolyte solution only in the regions in which the nanopores and the electrodes are connected, a configuration example in which a plurality of sample injection chambers are provided in a single device will be described. In this example, the description of the same configurations of the parallel ion current measuring device and the measuring kit as the configurations thereof in Example 1 is omitted, and only a configuration different from the configuration in Example 1, such as a configuration of the insulation forming mechanism, will be described.

Note that, in the solution chamber 430 in this example, the inlet port 108, the outlet port 110, and the partial partition walls 301 are provided as the insulation forming mechanism. In the parallel ion current measuring device illustrated in FIG. 1, the insulation forming mechanism includes the insulating material container 404, the valve 413, and the pump 401' in addition to the above members. However, the valve 413 and the pump 401' are not limited thereto as long as mechanisms having similar functions are provided.

FIG. 8 illustrates an example where plurality of sample injection chambers are provided in a single device. Although the sample injection chamber is not required to have a partition wall structure in measurement of an ion current as described above, it is possible to provide partition walls 111 and provide the electrodes 102 in respective divided regions. Provision of the plurality of sample injection chambers is effective in simultaneous measurement of a plurality of measurement target samples. In the case where plurality of samples are simultaneously measured, it is desirable to provide the independent inlet ports 107 and the independent outlet ports 109 for the respective solution chambers. FIG. 8 illustrates an example where a pair of an electrode and a nanopore is provided in the sample injection chamber. However, as described above, a plurality of combinations of the nanopores and the measurement electrodes may be provided with respect to a single sample-addition side electrode.

The embodiments of the invention have been described above, but the invention is not limited to the above examples and includes various modification examples. For example, the above examples have been described in detail for better understanding of the invention, and therefore the invention is not necessarily limited to the embodiments having all the configurations described above. Further, a part of a configuration of a certain example can be replaced with a configuration of another example, and a configuration of another example can be added to a configuration of a certain example. Further, another configuration can be added to, removed from, or replaced with a part of the configuration of each example.

REFERENCE SIGNS LIST

101 . . . sample injection chamber, 102, 105 . . . electrode, 103 . . . insulating membrane, 106 . . . independent measurement electrode chamber, 107, 108 . . . inlet port, 109, 110 . . . outlet port, 404 . . . insulating material container, 401, 401' . . . pump, 430 . . . solution chamber, 410, 411, 412, 413, 414 . . . valve, 451, 452 . . . region having high hydrophobicity, 453, 454 . . . region having high hydrophilicity, 301 . . . partial partition wall structure, 302 . . . electrode support structure

The invention claimed is:

1. A current measuring device, comprising:
    a first solution chamber including a plurality of first electrodes arranged to extend from outside of a first wall of the first solution chamber to inside of the first wall of the first solution chamber, wherein the first wall is located at a lower surface of the first solution chamber;
    a second solution chamber including a second electrode which is a counter electrode of the first electrodes, the second electrode being arranged to extend from outside of a second wall of the second solution chamber to inside of the second wall of the second solution chamber, wherein the second wall is located at an upper surface of the second solution chamber;
    a membrane provided between the first solution chamber and the second solution chamber, the membrane having a plurality of nanopores arranged in one-to-one correspondence with the plurality of first electrodes;
    a controller for applying a voltage between the first electrodes and the second electrode;
    a measuring kit for measuring a current flowing between the first electrodes and the second electrode via the nanopores by application of the voltage;

a container having a fluidic insulating material and connected to a first inlet port;

an insulator formed of solidified fluidic insulating material and disposed in the first solution chamber for insulating the first electrodes from each other in the first solution chamber in a state in which a conductive liquid is filled between the nanopores and the first electrodes;

wherein the first inlet port is disposed in a first side surface of the first solution chamber;

a second inlet port disposed in a first side surface of the second solution chamber;

a first outlet port disposed in a second side surface of the first solution chamber that is located at an opposite end of the first solution chamber from the first side surface of the first solution chamber; and a second outlet port disposed in a second side surface of the second solution chamber that is located at an opposite end of the second solution chamber from the first side surface of the second solution chamber.

2. The current measuring device according to claim 1, wherein the insulator is arranged in contact with a hydrophilic structure provided in the first solution chamber.

3. The current measuring device according to claim 1, wherein the insulator is arranged in contact with a hydrophobic structure provided in the first solution chamber.

4. The current measuring device according to claim 1, wherein the current measuring device includes partition walls provided around the nanopores in the first solution chamber, and regions located on paths directly connecting between the nanopores and the corresponding first electrodes are excluded by the partition walls from a region to be filled with the fluidic insulating material.

5. The current measuring device according to claim 1, wherein the current measuring device includes three-dimensional structures provided around the first electrodes in the first solution chamber, and regions located on paths directly connecting between the nanopores and the corresponding first electrodes are excluded by the three-dimensional structures from a region to be filled with the fluidic insulating material.

6. The current measuring device according to claim 1, wherein the plurality of first electrodes and the second electrode are arranged in the first and second solution chambers, respectively, such that the conductive liquid is in contact with an end surface and side surfaces of the plurality of first electrodes and the second electrode.

* * * * *